(12) United States Patent
Baughman et al.

(10) Patent No.: US 10,242,757 B2
(45) Date of Patent: Mar. 26, 2019

(54) PREDICTIVE WELLNESS MANAGEMENT

(71) Applicant: International Business Machines Corporation, Armonk, NY (US)

(72) Inventors: Aaron K. Baughman, Silver Spring, MD (US); Diwesh Pandey, Bangalore (IN); John P. Perrino, Hedgesville, WV (US); Todd R. Whitman, Bethany, CT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/910,193

(22) Filed: Mar. 2, 2018

(65) Prior Publication Data

US 2018/0374579 A1 Dec. 27, 2018

Related U.S. Application Data

(63) Continuation of application No. 15/631,169, filed on Jun. 23, 2017.

(51) Int. Cl.
| | | |
|---|---|---|
| *G16H 50/20* | (2018.01) | |
| *G16H 40/20* | (2018.01) | |
| *G16H 20/30* | (2018.01) | |
| *G09B 19/00* | (2006.01) | |
| *G06Q 10/06* | (2012.01) | |

(Continued)

(52) U.S. Cl.
CPC .......... *G16H 50/20* (2018.01); *A61B 5/0205* (2013.01); *G06Q 10/06* (2013.01); *G09B 19/0092* (2013.01); *G16H 20/30* (2018.01); *G16H 40/20* (2018.01); *G16H 50/50* (2018.01)

(58) Field of Classification Search
CPC ........ G16H 50/20; G16H 50/50; G16H 40/20; G16H 20/30; A61B 5/0205; G06Q 10/06; G09B 19/0092
See application file for complete search history.

(56) References Cited

U.S. PATENT DOCUMENTS

| 9,501,613 B1 | 11/2016 | Hanson et al. |
| 2008/0161733 A1 | 7/2008 | Einav |

(Continued)

FOREIGN PATENT DOCUMENTS

WO 2016115230 A1 7/2016

OTHER PUBLICATIONS

Baughman et al. Original U.S. Appl. No. 15/841,802, filed Dec. 14, 2017.

(Continued)

*Primary Examiner* — Eliza A Lam
(74) *Attorney, Agent, or Firm* — Stephen R. Yoder (57) ABSTRACT

Socially aware guidance and differential access controls within a control zone are determined for users based on individual wellness goals and predicted wellness patterns. Users are socially grouped based on wellness goals and predicted responsiveness to achieving the wellness goals. Biometric data obtained from users from social situations and activities provide insight into individual wellness progress and achievement of individual wellness goals. Predicted wellness patterns further assist users with achieving wellness goals through socially aware guidance and differential access controls.

1 Claim, 4 Drawing Sheets

(51) Int. Cl.
*G16H 50/50* (2018.01)
*A61B 5/0205* (2006.01)

(56) References Cited

U.S. PATENT DOCUMENTS

| | | | |
|---|---|---|---|
| 2012/0313776 A1* | 12/2012 | Utter, II | A61B 5/0205 340/539.12 |
| 2013/0268292 A1* | 10/2013 | Kim | G16H 20/10 705/2 |
| 2014/0125481 A1 | 5/2014 | Utter et al. | |
| 2014/0155705 A1 | 5/2014 | Papadopoulos et al. | |
| 2014/0330094 A1 | 11/2014 | Pacione et al. | |
| 2016/0034663 A1 | 2/2016 | Nino et al. | |
| 2016/0057565 A1* | 2/2016 | Gold | H04L 67/12 455/41.1 |
| 2016/0354637 A1 | 12/2016 | Zhang et al. | |
| 2017/0140049 A1* | 5/2017 | Chefalas | G06F 17/30867 |

OTHER PUBLICATIONS

Gibbons et al. "An Assessment of Alternatives for a National Computerized Criminal History System" Oct. 1982 NTIS order #PB83-166678. Library of Congress Catalog Card No. 82-600643 Washington, DC.

IP.com No. IPCOM000209084D:"Applying pattern keys to people control, particularly during emergence situations." IP.com Electronic Publication Date: Jul. 27, 2011. pp. 3.

IP.com No. IPCOM000243492D:"Method and System for Sensing Group State based on a Combination of Wearable Sensor Data." IP.com Electronic Publication Date: Sep. 24, 2015. pp. 4.

Appendix P List of IBM Patents or Applications Treated as Related. Dated Feb. 28, 2018. Two pages.

Baughman et al. Original U.S. Appl. No. 15/631,169, filed Jun. 23, 2017.

\* cited by examiner

PREDICTIVE WELLNESS MANAGEMENT

BACKGROUND

The present invention relates generally to the field of health technology, and more particularly to health and wellness management technology.

A habit is a routine of behavior that is repeated regularly and tends to occur subconsciously. Habits can be difficult to change or break. Unhealthy habits can have a negative impact on the wellness of an individual.

Biometric access control establishes access controls according to detected biometric information. Biometrics refers to metrics related to human characteristics. Biometrics authentication (or realistic authentication) is used in computer science as a form of identification and access control. It is also used to identify individuals within groups of people.

Biometric identifiers are distinctive, measurable characteristics used to label and describe individuals. Biometric identifiers are often categorized as physiological versus behavioral characteristics. Physiological characteristics are related to the shape of the body. Examples include: (i) fingerprint; (ii) palm veins; (iii) face recognition; (iv) DNA; (v) palm print; (vi) hand geometry; (vii) iris recognition; (viii) retina, and/or (ix) scent. Behavioral characteristics are related to the pattern of behavior of a particular individual, including, for example, typing rhythm, gait, and voice.

SUMMARY

According to an aspect of the present invention, there is a computer-implemented method, computer program product, and computer system for predicting wellness patterns that performs the following steps (not necessarily in the following order): (i) identifying a set of users within a specified region, each user having a set of individual wellness targets; (ii) receiving a set of biometric data for a sub-set of the users at a location within the specified region; (iii) forecasting a wellness pattern for the sub-set of users based on the set of biometric data; and (iv) responsive to is the forecasted wellness pattern for the sub-set of users at the location, adjusting an access control for an object within the location.

DETAILED DESCRIPTION

Socially aware guidance and differential access controls within a control zone are determined for users based on individual wellness goals and predicted wellness patterns. Users are socially grouped based on wellness goals and predicted responsiveness to achieving the wellness goals. Biometric data obtained from users from social situations and activities provide insight into individual wellness progress and achievement of individual wellness goals. Predicted wellness patterns further assist users with achieving wellness goals through socially aware guidance and differential access controls. This Detailed Description section is divided into the following sub-sections: (i) Hardware and Software Environment; (ii) Example Embodiment; (iii) Further Comments and/or Embodiments; and (iv) Definitions.

I. Hardware and Software Environment

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
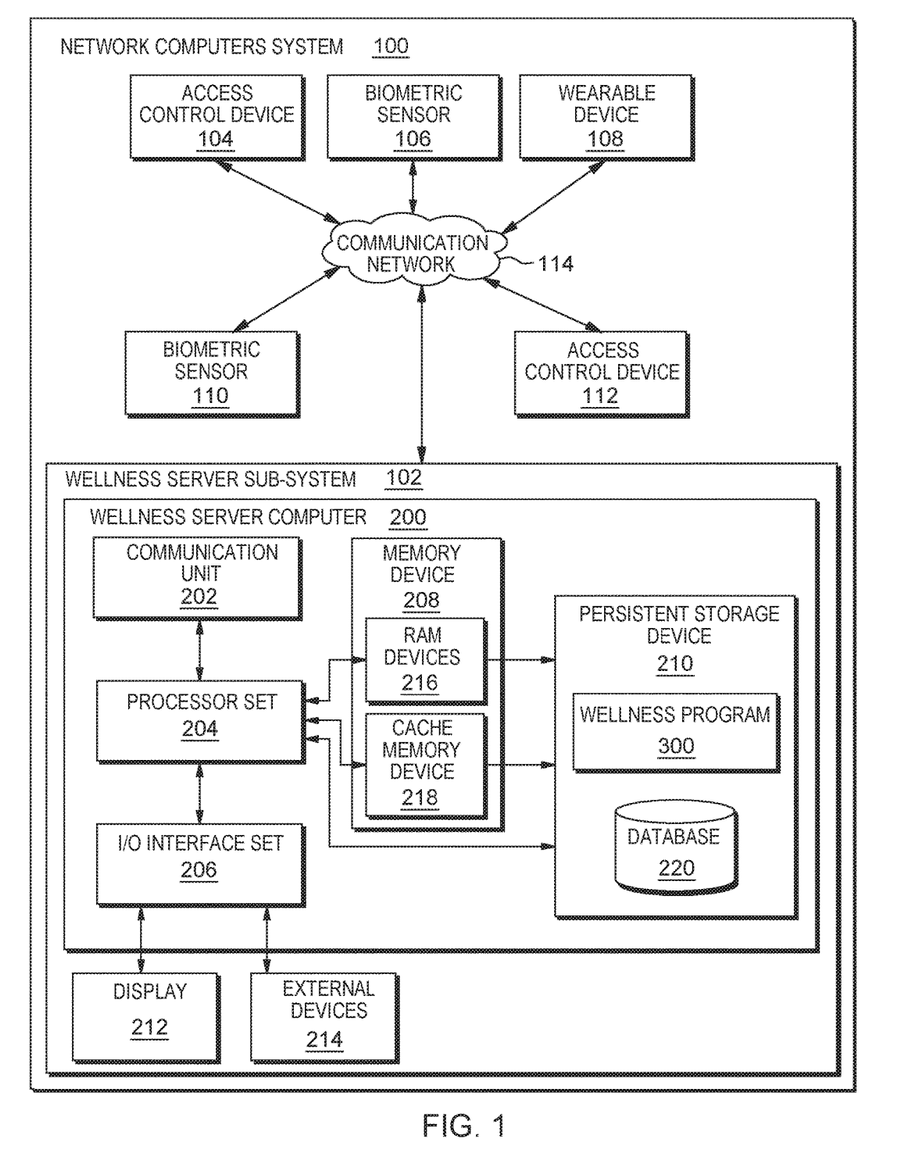
FIG. 1 is a block diagram view of a first embodiment of a system according to the present invention.

An embodiment of a possible hardware and software environment for software and/or methods according to the present invention will now be described in detail with reference to the Figures. FIG. 1 is a functional block diagram illustrating various portions of networked computers system 100, including: wellness server sub-system 102; access control device 104, biometric sensor 106, wearable device 108, biometric sensor 110, access control device 112; and communication network 114. Wellness server sub-system 102 contains: wellness server computer 200; display device 212; and external devices 214. Wellness server computer 200 contains: communication unit 202; processor set 204; input/output (I/O) interface set 206; memory device 208; and persistent storage device 210. Memory device 208 contains: random access memory (RAM) devices 216; and cache memory device 218. Persistent storage device 210 contains: wellness program 300 and database 220.

Wellness server sub-system 102 is, in many respects, representative of the various computer sub-systems in the present invention. Accordingly, several portions of wellness server sub-system 102 will now be discussed in the following paragraphs.

Wellness server sub-system 102 may be a laptop computer, a tablet computer, a netbook computer, a personal computer (PC), a desktop computer, a personal digital assistant (PDA), a smart phone, or any programmable electronic device capable of communicating with client sub-systems via communication network 114. Wellness program 300 is a collection of machine readable instructions and/or data that is used to create, manage, and control certain software functions that will be discussed in detail, below, in the Example Embodiment sub-section of this Detailed Description section.

Wellness server sub-system 102 is capable of communicating with other computer sub-systems via communication network 114. Communication network 114 can be, for example, a local area network (LAN), a wide area network (WAN) such as the Internet, or a combination of the two, and can include wired, wireless, or fiber optic connections. In general, communication network 114 can be any combination of connections and protocols that will support communications between server and client sub-systems.

Wellness server sub-system 102 is shown as a block diagram with many double arrows. These double arrows (no separate reference numerals) represent a communications fabric, which provides communications between various components of wellness server sub-system 102. This communications fabric can be implemented with any architecture designed for passing data and/or control information between processors (such as microprocessors, communications processors, and/or network processors, etc.), system memory, peripheral devices, and any other hardware components within a system. For example, the communications fabric can be implemented, at least in part, with one or more buses.

Memory device 208 and persistent storage device 210 are computer readable storage media. In general, memory device 208 can include any suitable volatile or non-volatile computer readable storage media. It is further noted that, now and/or in the near future: (i) external devices 214 may be able to supply some, or all, memory for wellness server sub-system 102; and/or (ii) devices external to wellness server sub-system 102 may be able to provide memory for wellness server sub-system 102.

Wellness program 300 is stored in persistent storage device 210 for access and/or execution by one or more processors of processor set 204, usually through memory device 208. Persistent storage device 210: (i) is at least more persistent than a signal in transit; (ii) stores the program (including its soft logic and/or data) on a tangible medium (such as magnetic or optical domains); and (iii) is substantially less persistent than permanent storage. Alternatively, data storage may be more persistent and/or permanent than the type of storage provided by persistent storage device 210.

Wellness program 300 may include both substantive data (that is, the type of data stored in a database) and/or machine readable and performable instructions. In this particular embodiment (i.e., FIG. 1), persistent storage device 210 includes a magnetic hard disk drive. To name some possible variations, persistent storage device 210 may include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage device 210 may also be removable. For example, a removable hard drive may be used for persistent storage device 210. Other examples include optical and magnetic disks, thumb drives, and smart cards that are inserted into a drive for transfer onto another computer readable storage medium that is also part of persistent storage device 210.

Communication unit 202, in these examples, provides for communications with other data processing systems or devices external to wellness server sub-system 102. In these examples, communication unit 202 includes one or more network interface cards. Communication unit 202 may provide communications through the use of either or both physical and wireless communications links. Any software modules discussed herein may be downloaded to a persistent storage device (such as persistent storage device 210) through a communications unit (such as communication unit 202).

I/O interface set 206 allows for input and output of data with other devices that may be connected locally in data communication with wellness server computer 200. For example, I/O interface set 206 provides a connection to external devices 214. External devices 214 will typically include devices, such as a keyboard, a keypad, a touch screen, and/or some other suitable input device. External devices 214 can also include portable computer readable storage media, such as, for example, thumb drives, portable optical or magnetic disks, and memory cards. Software and data used to practice embodiments of the present invention (e.g., wellness program 300) can be stored on such portable computer readable storage media. In these embodiments, the relevant software may (or may not) be loaded, in whole or in part, onto persistent storage device 210 via I/O interface set 206. I/O interface set 206 also connects in data communication with display device 212.

Display device 212 provides a mechanism to display data to a user and may be, for example, a computer monitor or a smart phone display screen.

The programs described herein are identified based upon the application for which they are implemented in a specific embodiment of the invention. However, it should be appreciated that any particular program nomenclature herein is used merely for convenience, and thus, the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

Figure 2:
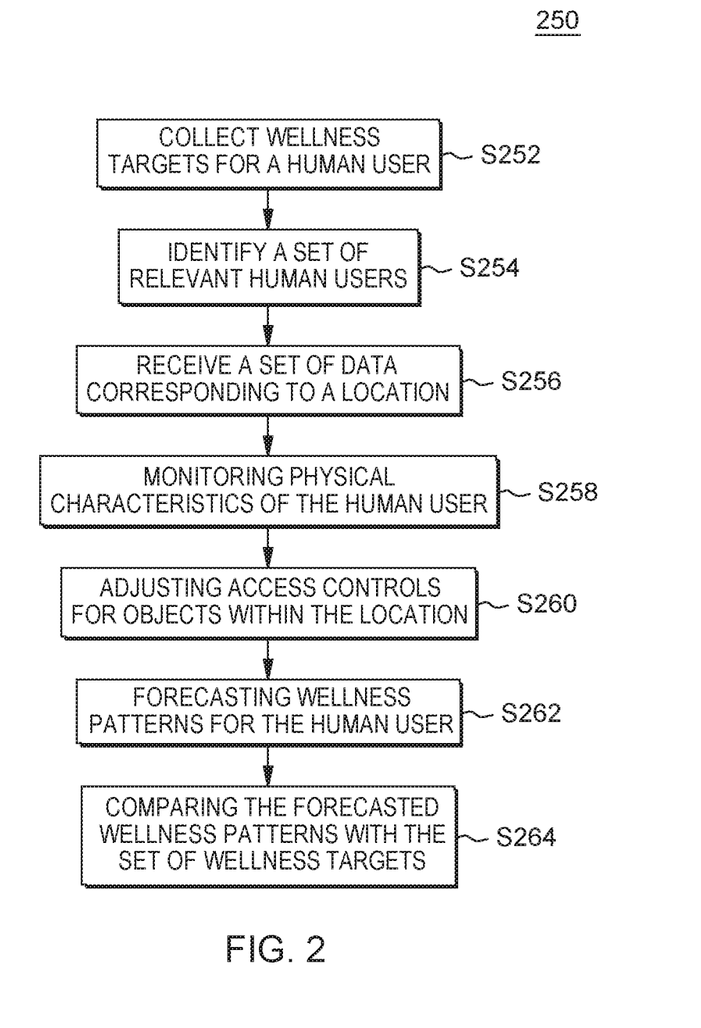
FIG. 2 is a flowchart showing a first embodiment method performed, at least in part, by the first embodiment system.
Figure 3:
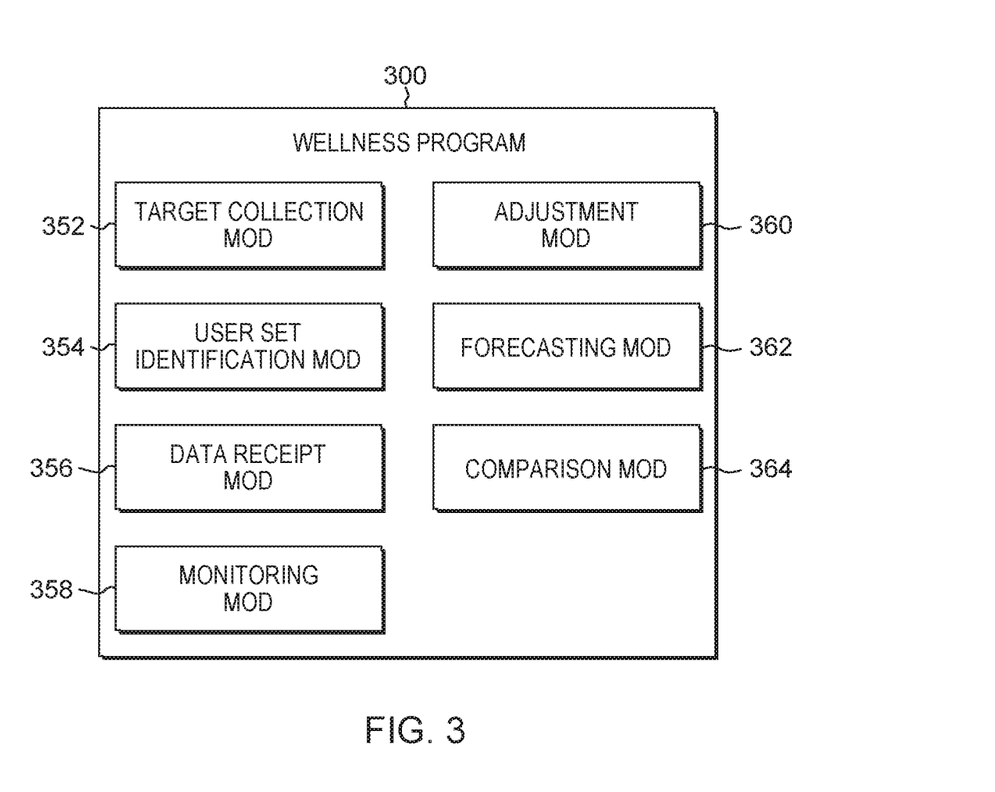
FIG. 3 is a block diagram view of a machine logic (e.g., software) portion of the first embodiment system.

FIG. 2 shows flowchart 250 depicting a method according to the present invention. FIG. 3 shows wellness program 300, which performs at least some of the method operations of flowchart 250. This method and associated software will now be discussed, over the course of the following paragraphs, with extensive reference to FIG. 2 (for the method operation blocks) and FIG. 3 (for the software blocks).

Processing begins at operation S252, where target collection module ("mod") 352 collects wellness targets for a human user. In this example embodiment, a human user is supported to achieve certain wellness targets while associating with other human users and/or objects within a particular zone where biometric data of the user is collected and/or access to objects is controlled. Wellness targets are achievable personal goals tailored to the human user's life. Wellness targets are designed to maintain positive behaviors exhibited by the human user or alter negative behaviors exhibited by the human user. Wellness targets may include goals for any facet of wellness, such as social wellness, emotional wellness, intellectual wellness, and physical wellness. Wellness targets may be inputted to wellness program 300 by the human user, a physician, a therapist, an employer, family members or friends of the human user, or any other relevant third party. In this embodiment, human user Abe visited a physician and was recommended to decrease strenuous physical activity by Abe's right arm because of an injury. Wellness program 300 may collect the wellness target of 'decreasing right arm use' directly from Abe's physician, directly from Abe, or from the physician's medical report to Abe.

Processing proceeds to operation S254, where user set identification mod 354 identifies a set of other human users relevant to the human user's wellness target. A set of human users are identified to reinforce positive behaviors by the human user. The human users identified by wellness program 300 have similar biometric data, have similar wellness targets, and/or provide an indicator that shows strengthening of positive behaviors from users around them. The human user set are identified in a manner to exclude sharply antagonistic users. The human user set may also include mildly antagonistic users and users with opposing tendencies in a limited interaction basis to assimilate different ideas into a larger group. The set of other human users may change periodically based on each user's individual goals and behavior. In this embodiment, wellness program 300 identifies a set of human users who would positively influence Abe to meet his wellness target. Users with a propensity toward strenuous physical activity using their arms, such as weightlifters or rock climbers, are excluded from the set. Users who maintain an active lifestyle while not utilizing their arms as much, such as cyclists or joggers, are included in the set for Abe. Users who also have suffered an injury to an appendage are included in the set of relevant users.

Processing proceeds to operation S256, where data receipt mod 356 receives a set of data corresponding to a location. As the human user progresses through the human user's daily life, data corresponding to locations that the human user has traveled to or will travel to in the future are stored in database 220, as shown on FIG. 1. Data corresponding to a location includes geospatial information, weather forecasts, current events calendars, noise level, and data regarding other users in the location's vicinity. Inputs from sensors may capture the identity of objects and other users inside the location. Users in a location may be identified by biometric information as well as GPS registration through wellness program 300. In this embodiment, Abe travels to a local gymnasium for some exercise. Wellness program 300 collects data on the gym such as, room temperature, gym activities schedule, and information on the current patrons in the gym. Wellness program would, for example, collect information from the gym's web site regarding times for group cycling classes and other physical activities that do not require strenuous arm usage.

Processing proceeds to operation S258, where monitoring mod monitors the human user's physical characteristics. Human users may wear sensory devices (or biometric sensors 106 and 110 as seen in FIG. 1) on their person that monitors certain physical characteristics. Physical characteristics include monitoring body temperature, heart rate, respiration, physical movement, and brain waves. These monitored physical characteristics are used to gauge the wellness of a user at a specific time. In this embodiment, Abe is wearing sensors on his injured right arm that detect physical movement as well as sensors that monitor his vital signs such as heart rate. For example, if Abe decides to lift weights with his right arm, the sensors that Abe is wearing would detect the physical movement done by his arm. Sensors monitoring Abe's heart rate, respiration, pupil dilation, and body movement may also detect arm pain or discomfort from strenuous physical activity.

Processing proceeds to operation S260, where adjustment mod 360 adjusts access controls for objects within the location. Based on the human user's wellness targets, access controls are adjusted for the human user. As shown in FIG. 1, wearable device 108 like an optical head-mounted display may be worn by the human user to provide indicators to attract or deter the user to certain locations and activities. Certain locations may also provide physical access controls (or access control devices 104 and 112 as seen in FIG. 1) to doors and drawers to encourage or discourage human users to utilize their contents. If certain objects within a drawer are detrimental to a wellness target of a human user, mechanisms may be in place that allow for the drawer to be more difficult for the human user to open it. In this embodiment, Abe is wearing an optical head-mounted display in the gym that has certain access controls programmed to respond to wellness program 300. The optical head-mounted display provides indicators to Abe to avoid strenuous physical arm activities such as the weight rack and provides indicators to Abe to point him toward physical exercise that does not strain his right arm such as the cycling room. The door to the free weights room in the gym may be selectively operated to be more rigid and have more resistance so that it is difficult for Abe to access the weights inside.

Processing proceeds to operation S262, where forecasting mod 362 forecasts wellness patterns for the human user. Wellness patterns are continued good habits performed by a human user over time. Physical characteristics, such as respiration, skin temperature, pulse, facial expressions, and walking gait, are used to forecast wellness patterns. These factors are regressed over a period of time to determine trending patterns and project into the future the sinusoidal shape of regression, base factors, and spikes in motion from social interactions. Spikes occur with different social interactions, so personality of interaction and reaction is measured. Extroverted and introverted tendencies over a period of time for a given interaction along with current physical characteristics presents a wellness pattern. The base factors and spikes in predictions from social interactions within a group of users gives a wellness pattern for the social group as a whole. In this embodiment, wellness program 300 forecasts wellness patterns for Abe over a period of time as he deals with his injured arm. Based on Abe's preferred activities and his preferred areas of socialization along with the physical characteristics that he has presented, wellness program 300 forecasts future interactions with users Baker and Charlie. Baker and Charlie are both active weightlifters. Wellness program 300 forecasts Abe would likely utilize his injured right arm if associated with Baker and Charlie. Wellness program 300 also forecasts future interactions with users David and Elizabeth. David and Elizabeth are both active cyclists. Wellness program 300 forecasts Abe would likely not utilize his injured right arm if associated with David and Elizabeth.

Processing proceeds to operation S264, where comparison mod 364 compares the forecasted wellness patterns with the set of wellness targets. Based off predicted outcomes of associations with other users and locations, wellness program 300 provides indicators and adjusts access control for the human user. These indicators and access control adjustments are used to align the human user more toward the corresponding wellness target after predicted changes are taken into consideration. In this embodiment, Abe is provided indicators via the optical head-mounted display and access controls to avoid Baker and Charlie and to associate with David and Elizabeth. Indicators shown to Abe point him to locations where David and Elizabeth are located and where Baker and Charlie are not located.

III. Further Comments and/or Embodiments

Some embodiments of the present invention recognize the following facts, potential problems, and/or potential areas for improvement with respect to the current state of the art. Unhealthy or bad habits can be difficult to change or break that is contrary to overall health. Often, bad habits are the result of association or continued association with social structures. However, leaving a social structure is a foreign concept to many and guidance is often needed to direct an individual to make better choices. If a group of people interact with each other closely, they often have a general and homogenous view on things. Finding a group of people or a set of activities that benefit a person with something specific is difficult.

Figure 4:
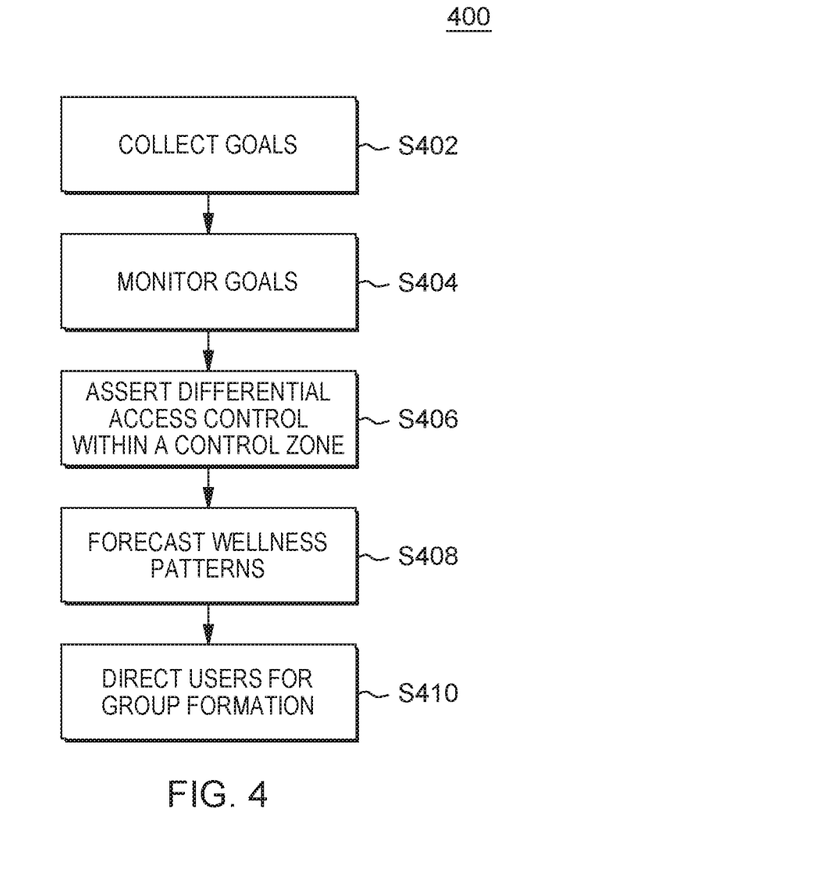
FIG. 4 is a flowchart showing a second embodiment method performed, at least in part, by the first embodiment system.

FIG. 4 shows flowchart 400 depicting a method according to an embodiment of the present invention. The method may be implemented by a wellness program such as illustrated in FIG. 1 at wellness server sub-system 100. This method will now be discussed, over the course of the following paragraphs, with extensive reference to FIG. 4 for the method operation blocks.

Processing begins at step S402, where positive behavior goals are collected. In this example, positive behavior goals are collected for each user within an interior space, such as a hospital, office building, or living space.

Processing proceeds to step S404, where the positive behavior goals are monitored. Each user within the interior space is monitored for individual biometric data. The collected biometric data is correlated to the positive behavior goals in support of a determination regarding, for example, achievement of a positive behavior goal or progress toward or away from a particular positive behavior goal.

Processing proceeds to step S406, where differential access control is asserted within the interior space. In this example, objects within the interior space are programmed for differential access control. For each individual in the space, certain access controls are determined according to their positive behavior goals. The locations of users within the space are determined periodically for the purpose of differential access control to the objects, such as cabinets, rooms, or secure portions of the interior space.

Processing proceeds to step S408, where wellness patterns for the users are forecast based on the positive behavior goals. In this example, the set of all users have a combined wellness pattern based on received biometric data correlated to the individual positive behavior goals. The combined wellness pattern is forecast according a predetermined set of historic data, such as for the last 8 hours, 24 hours, or week. Alternatively, individual wellness patterns are predicted, or forecast, with respect to the positive behavior goals of a user. The forecasted pattern indicates progress toward or away from particular positive behavior goals.

Processing proceeds to step S410, where the users are directed to take an action corresponding to group formation based on a forecasted wellness pattern. In this example, the combined wellness pattern is the basis for directing group formation. Alternatively, individual wellness patterns are the basis for individual direction as to group formation. In some embodiments, certain users are grouped together and certain users remain isolated from a group.

Some embodiments of the present invention may include one, or more, of the following features, characteristics, and/or advantages. Eating behaviors, physical training or emotional wellness can be guided by encouraging positive behaviors through access control and direction. Access control to areas within a structure such as a home is automatically controlled to augment the cognition of the human. Items that would help or complement a goal are easily accessible while those that are not are more difficult to find and use or consume. Big data analysis of streaming features about an individual are used to provide predictions and simulations to determine where a person would emerge. If multiple people are within the same cognitive structure, they are gently moved apart or joined in accordance with their state. Users are guided by the cognitive system by directing and access control.

IV. Definitions

"Present invention" does not create an absolute indication and/or implication that the described subject matter is covered by the initial set of claims, as filed, by any as-amended set of claims drafted during prosecution, and/or by the final set of claims allowed through patent prosecution and included in the issued patent. The term "present invention" is used to assist in indicating a portion or multiple portions of the disclosure that might possibly include an advancement or multiple advancements over the state of the art. This understanding of the term "present invention" and the indications and/or implications thereof are tentative and provisional and are subject to change during the course of patent prosecution as relevant information is developed and as the claims may be amended.

"Embodiment," see the definition for "present invention."

"And/or" is the inclusive disjunction, also known as the logical disjunction and commonly known as the "inclusive or." For example, the phrase "A, B, and/or C," means that at least one of A or B or C is true; and "A, B, and/or C" is only false if each of A and B and C is false.

A "set of" items means there exists one or more items; there must exist at least one item, but there can also be two, three, or more items. A "subset of" items means there exists one or more items within a grouping of items that contain a common characteristic.

A "plurality of" items means there exists at more than one item; there must exist at least two items, but there can also be three, four, or more items.

"Includes" and any variants (e.g., including, include, etc.) means, unless explicitly noted otherwise, "includes, but is not necessarily limited to."

A "user" or a "subscriber" includes, but is not necessarily limited to: (i) a single individual human; (ii) an artificial intelligence entity with sufficient intelligence to act in the place of a single individual human or more than one human; (iii) a business entity for which actions are being taken by a single individual human or more than one human; and/or (iv) a combination of any one or more related "users" or "subscribers" acting as a single "user" or "subscriber."

The terms "receive," "provide," "send," "input," "output," and "report" should not be taken to indicate or imply, unless otherwise explicitly specified: (i) any particular degree of directness with respect to the relationship between an object and a subject; and/or (ii) a presence or absence of a set of intermediate components, intermediate actions, and/or things interposed between an object and a subject.

A "module" is any set of hardware, firmware, and/or software that operatively works to do a function, without regard to whether the module is: (i) in a single local proximity; (ii) distributed over a wide area; (iii) in a single proximity within a larger piece of software code; (iv) located within a single piece of software code; (v) located in a single storage device, memory, or medium; (vi) mechanically connected; (vii) electrically connected; and/or (viii) connected in data communication. A "sub-module" is a "module" within a "module."

A "computer" is any device with significant data processing and/or machine readable instruction reading capabilities including, but not necessarily limited to: desktop computers; mainframe computers; laptop computers; field-programmable gate array (FPGA) based devices; smart phones; personal digital assistants (PDAs); body-mounted or inserted computers; embedded device style computers; and/or application-specific integrated circuit (ASIC) based devices.

"Electrically connected" means either indirectly electrically connected such that intervening elements are present or directly electrically connected. An "electrical connection" may include, but need not be limited to, elements such as capacitors, inductors, transformers, vacuum tubes, and the like.

"Mechanically connected" means either indirect mechanical connections made through intermediate components or direct mechanical connections. "Mechanically connected" includes rigid mechanical connections as well as mechanical connection that allows for relative motion between the mechanically connected components. "Mechanically connected" includes, but is not limited to: welded connections;

solder connections; connections by fasteners (e.g., nails, bolts, screws, nuts, hook-and-loop fasteners, knots, rivets, quick-release connections, latches, and/or magnetic connections); force fit connections; friction fit connections; connections secured by engagement caused by gravitational forces; pivoting or rotatable connections; and/or slidable mechanical connections.

A "data communication" includes, but is not necessarily limited to, any sort of data communication scheme now known or to be developed in the future. "Data communications" include, but are not necessarily limited to: wireless communication; wired communication; and/or communication routes that have wireless and wired portions. A "data communication" is not necessarily limited to: (i) direct data communication; (ii) indirect data communication; and/or (iii) data communication where the format, packetization status, medium, encryption status, and/or protocol remains constant over the entire course of the data communication.

The phrase "without substantial human intervention" means a process that occurs automatically (often by operation of machine logic, such as software) with little or no human input. Some examples that involve "no substantial human intervention" include: (i) a computer is performing complex processing and a human switches the computer to an alternative power supply due to an outage of grid power so that processing continues uninterrupted; (ii) a computer is about to perform resource intensive processing and a human confirms that the resource-intensive processing should indeed be undertaken (in this case, the process of confirmation, considered in isolation, is with substantial human intervention, but the resource intensive processing does not include any substantial human intervention, notwithstanding the simple yes-no style confirmation required to be made by a human); and (iii) using machine logic, a computer has made a weighty decision (for example, a decision to ground all airplanes in anticipation of bad weather), but, before implementing the weighty decision the computer must obtain simple yes-no style confirmation from a human source.

"Automatically" means "without any human intervention."

The term "real time" (and the adjective "real-time") includes any time frame of sufficiently short duration as to provide reasonable response time for information processing as described. Additionally, the term "real time" (and the adjective "real-time") includes what is commonly termed "near real time," generally any time frame of sufficiently short duration as to provide reasonable response time for on-demand information processing as described (e.g., within a portion of a second or within a few seconds). These terms, while difficult to precisely define, are well understood by those skilled in the art.

What is claimed is:

1. A computer implemented method for predicting wellness patterns, the computer-implemented method comprising:

determining a set of individual wellness targets for a set of users;

identifying a subset of users within a physical structure, each user having a common individual wellness target;

receiving a set of biometric data for the subset of users during social situations and activities performed within the physical structure;

storing individual biometric data corresponding to each user in the subset of users;

monitoring the subset of the users for physical characteristics including heart rate, physical movement, and brain wave activity;

determining a first physical characteristic of a first user and a second physical characteristic of a second user, the first physical characteristics being equivalent to the second physical characteristics;

storing a set of physical characteristics corresponding to each user in the subset of users;

determining, for each user in the subset of users, a set of physical characteristic trends based on the heart rate, physical movement, and brain wave activity;

forecasting a wellness pattern for the subset of users based on the set of biometric data and each set of physical characteristics trends, the wellness pattern specifying a predicted heart rate and a predicted physical activity;

responsive to the forecasted wellness pattern for the subset of users, adjusting an access control for a door in the physical structure, the door securing an enclosure, the second user located within the enclosure, the adjusting action allowing the first user to access the enclosure based on the first physical characteristic, the second physical characteristic, and corresponding biometric data of the first user and the second user;

monitoring the subset of the users for a second set of physical characteristics including heart rate, physical movement, and brain wave activity; and comparing the wellness pattern with the second set of physical characteristics to determine achievement of the set of individual wellness targets.

* * * * *